US00PP09015P

United States Patent [19]

Zary

[11] Patent Number: Plant 9,015

[45] Date of Patent: Dec. 20, 1994

[54] MINIATURE ROSE PLANT NAMED JACPOY

[75] Inventor: Keith W. Zary, Thousand Oaks, Calif.

[73] Assignee: Bear Creek Gardens, Inc., Medford, Oreg.

[21] Appl. No.: 209,455

[22] Filed: Mar. 11, 1994

[51] Int. Cl.[5] ..... A01H 5/00

[52] U.S. Cl. ..... Plt./7.1

[58] Field of Search ..... Plt. 7.1, 10, 10.1, Plt. 22

*Primary Examiner*—Howard J. Locker

*Attorney, Agent, or Firm*—Klarquist, Sparkman, Campbell, Leigh & Whinston

[57] ABSTRACT

Miniature rose plant having compact, quite rounded growth habit; bright-colored, distinctive, small, hybrid-tea-shaped blooms; large flower clusters; and small, dark green, disease-resistant foliage.

1 Drawing Sheet

The present invention relates to a new and distinct variety of rose plant of the miniature class that was originated by me by crossing two unnamed seedlings, each of which was the result of crossing unnamed seedlings.

The primary objective of this breeding was to produce a new rose variety having the bright orange with yellow reverse flower color and hybrid tea-shaped bloom of the female parent combined with the miniature plant habit and large flower clusters of the male parent. The objective was substantially achieved, along with other desirable improvements, as evidenced by the following unique combination of characteristics that are outstanding in the new variety and that distinguish it from its parents, as well as from all other varieties of which I am aware:

1. Small, yellow and orange-red flowers presented in large clusters;
2. Compact growth habit;
3. Small, dark green, disease-resistant foliage; and
4. Hybrid-tea-shaped blooms.

Asexual reproduction of this new variety by softwood cuttings as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling.

*Pollen parent.*—Unnamed seedling.

Classification:

*Botanical.*—*Rosa hybrida.*

*Commercial.*—Miniature.

FLOWER

Observations made from specimens grown in a garden environment in Somis, Calif., from May through October, 1993.

Blooming habit: Recurrent.

Bud:

*Size.*—16 mm long when the petals start to unfurl.

*Form.*—Short, pointed ovoid.

*Color.*—When sepals first divide, color is a blend of Yellow-Orange Group 21C, Red Group 43C and Orange-Red Group 34C. When half blown, the upper sides of the petals are Orange-Red Group 33A on the upper portion and Yellow-Orange Group 21C on the lower portion, and the lower sides of the petals are Red Group 43C on the upper portion, and Yellow-Orange Group 21C on the lower portion.

*Sepals.*—Color: Green Group 138B with a reddish cast (Greyed Red Group 182A). Surface texture: Covered in fine hairs. There are three normally appendaged sepals and two unappendaged sepals with hairy edges.

*Receptacle.*—Color: Green Group 138B. Shape: Funnel. Size: Small (6 mm×6 mm). Surface: Hairy.

*Peduncle.*—Length: Short (38 mm). Surface: Glandular. Color: Light green and often bronzy. Strength: Stiff, erect; slender.

Bloom:

*Size.*—Small. Average open size is 50 mm to 64 mm in diameter.

*Borne.*—Singly and several together in rounded clusters of 3 to 7 flowers.

*Stems.*—Short (15 cm to 20 cm), strong.

*Form.*—When first open: High centered. Permanence: Retains its form to the end; outer petals curl back, quill fashion.

*Petalage.*—Number of petals under normal conditions: 30 to 35.

*Color.*—The upper side of the petals is Orange-Red Group 33A on the upper portion and Yellow-Orange Group 21C on the lower portion. The reverse side of the petals is Red Group 43C on the upper portion and Yellow-Orange Group 21C on the lower portion. The base of the petals is Yellow-Orange Group 21C. The major color on the upper side is Red-Orange Group 33A.

*Variegations.*—None.

*Discoloration.*—The general tonality at the end of the first day: No change. At the end of the third day, loss of color intensity, with gradual change, especially on the outer petals, to Red Group 54B.

*Fragrance.*—Slight.

Petals:

*Texture.*—Thick.

*Shape.*—Deltoid.

*Form.*—Tips are slightly recurved and edges slightly quilled.

*Arrangement.*—Imbricated, with few petaloids in the center.

*Persistance.*—Drop off cleanly.

*Lastingness.*—On the plant: Fair (5 days). As a cut flower: Fair (5 to 6 days).

Reproductive parts:

*Anthers.*—Size: Medium. Quantity: Many. Color: Yellow. Arrangement: Regular around styles.

*Filaments.*—Color: Yellow.

*Pollen.*—Color: Gold yellow.

*Styles.*—Color: Red.

*Stigmas.*—Color: Greenish white.

Form: Bush.

Growth: Vigorous, dwarf, upright, branching. Average size is 40 to 60 cm tall by 40 cm wide.

Foliage:

*Number of leaflets on normal mid-stem leaves.*—5 or 7.

*Size.*—Small.

*Quantity.*—Abundant.

*Color.*—New foliage: Reddish (Greyed Red Group 183A). Old foliage: Dark green (Green Group 139A).

Leaflets:

*Shape.*—Pointed oval.

*Texture.*—Upper side: Leathery, glossy.

*Edge.*—Serrated.

*Serration.*—Single and small.

*Petiole rachis.*—Color: Green.

*Petiole underside.*—Smooth, with occasional prickles.

*Stipules.*—Long (12 to 19 mm) and bearded.

*Disease resistance.*—Resistant to mildew and rust under normal growing conditions at Somis, Calif.

Wood:

*New wood.*—Color: Light green. Bark: Smooth.

*Old wood.*—Color: Green. Bark: Smooth.

Prickles:

*Quantity.*—Ordinary on main canes from base. Ordinary on laterals from main canes.

*Form.*—Medium (10 mm), hooked slightly downward.

*Color when young.*—Red, turning green very quickly.

Small prickles:

*Quantity.*—None on main stalks. None on laterals.

I claim:

1. A new and distinct variety of rose plant of the miniature class, substantially as herein shown and described, characterized particularly as to novelty by the unique combination of its compact, quite rounded growth habit; bright-colored, distinctive, small, hybrid-tea-shaped blooms; large flower clusters; and small, dark green, disease-resistant foliage.

* * * * *

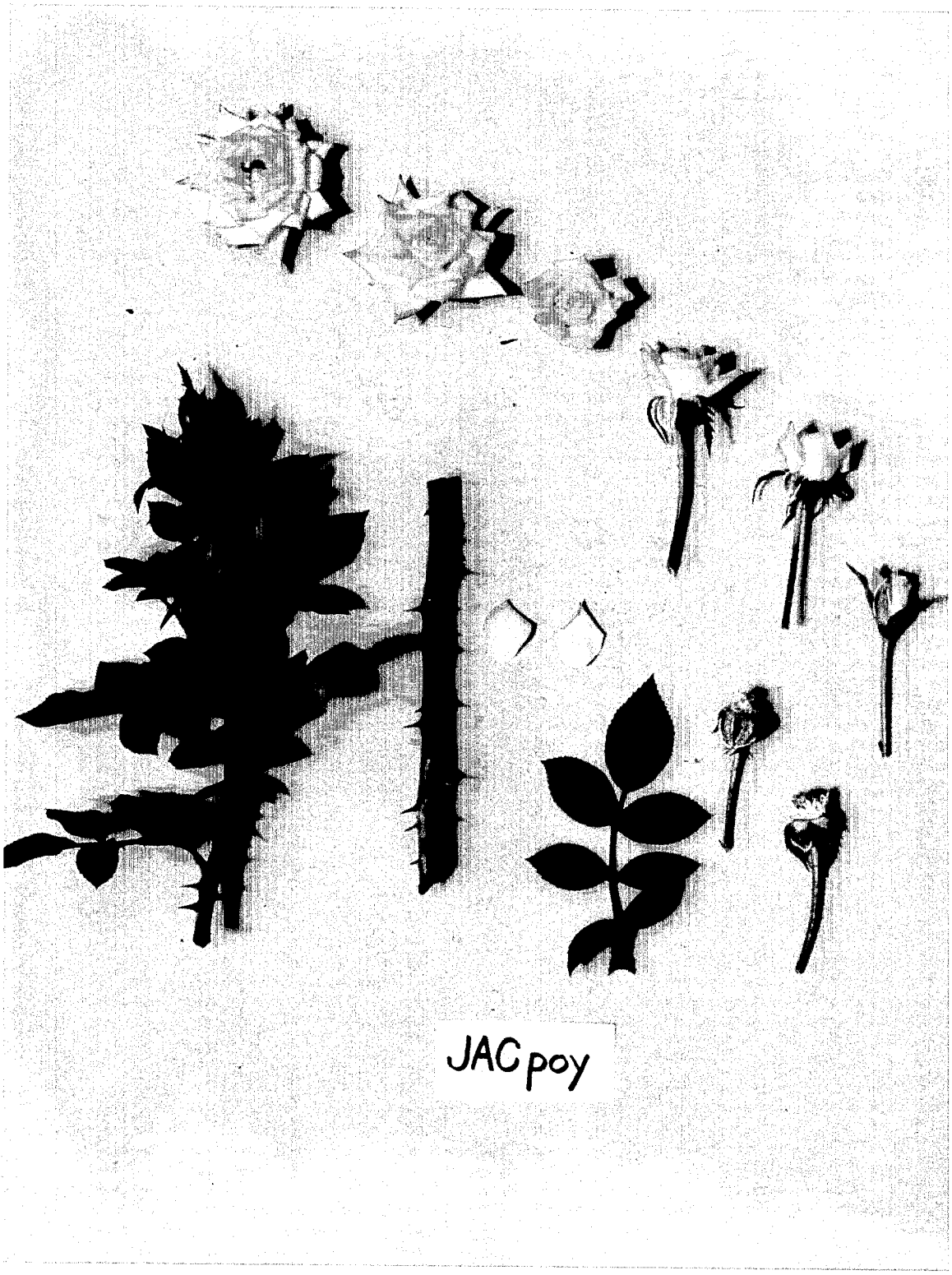
JACpoy